(12) United States Patent
Moore

(10) Patent No.: US 6,513,928 B1
(45) Date of Patent: Feb. 4, 2003

(54) SPORTS TRAINING EYEGLASSES

(76) Inventor: Gregory S. Moore, Rte. 2, Box 129, Sandyville, WV (US) 25275

( * ) Notice: Subject to any disclaimer, the term of this patent is extended or adjusted under 35 U.S.C. 154(b) by 383 days.

(21) Appl. No.: 10/030,391

(22) PCT Filed: Jul. 6, 2000

(86) PCT No.: PCT/US00/18470

§ 371 (c)(1),
(2), (4) Date: Jan. 4, 2002

(87) PCT Pub. No.: WO01/02898

PCT Pub. Date: Jan. 11, 2001

Related U.S. Application Data

(60) Provisional application No. 60/142,357, filed on Jul. 6, 1999.

(51) Int. Cl.[7] .................................................. G02C 5/20
(52) U.S. Cl. ......................... 351/118; 351/46; 351/107; 473/210
(58) Field of Search ............................... 351/41, 44, 46, 351/47, 103, 105–107, 109, 111, 114, 118, 120, 121, 124, 130, 178, 204; 473/210

(56) References Cited

U.S. PATENT DOCUMENTS

| | | | | | |
|---|---|---|---|---|---|
| 3,555,563 A | * | 1/1971 | Grossman | ..................... | 351/46 |
| 4,022,475 A | * | 5/1977 | Todd | ..................... | 273/183 B |
| 4,787,727 A | * | 11/1988 | Boodman et al. | ........... | 351/118 |
| 5,289,592 A | * | 3/1994 | Paivarinta | ................... | 351/119 |
| 5,675,398 A | * | 10/1997 | Moore | ......................... | 351/46 |

* cited by examiner

Primary Examiner—Huy Mai
(74) Attorney, Agent, or Firm—Steptoe & Johnson PLLC

(57) ABSTRACT

A pair of sports training eyeglasses is provided for training a user to keep his/her eye on a ball while hitting either a stationary ball, e.g. in golf or hockey, or a moving ball, e.g., in baseball and softball. The pair of sports training eyeglasses have a pair of lenses, each lens having an opaque peripheral region and a viewing aperture, and a frame having an elongated bridge bar having opposite ends, a pair of opposing temporal side members extending from respective ends of the elongated bridge bar, a means for adjusting the position of each temporal side member in relation to the elongated bridge bar, a movably nose piece, a means for removably attaching each lens to the elongated bridge bar, wherein the position of each lens is adjustable in relation to the nose piece, and a means for locking the position of each lens on the elongated bridge bar. A first set of lenses is provided having an oval shaped viewing aperture and is used in training a user to hit a moving ball. A second set of lenses is provided having a viewing aperture being an elongated slit that is rotatable between a vertical orientation for fitting the lenses on a user and a horizontal orientation for training the user to hit a stationary ball. A method is also provided wherein a user adjusts the pair of eyeglasses to a comfortable fit, wears the pair of eyeglasses, adjusts the position of the lenses, locks the position of the lenses, and trains in hitting either a moving ball or a stationary ball depending on whether the first set of lenses or the second set of lenses are installed, respectively.

26 Claims, 9 Drawing Sheets

FIG. 2
FIG. 3
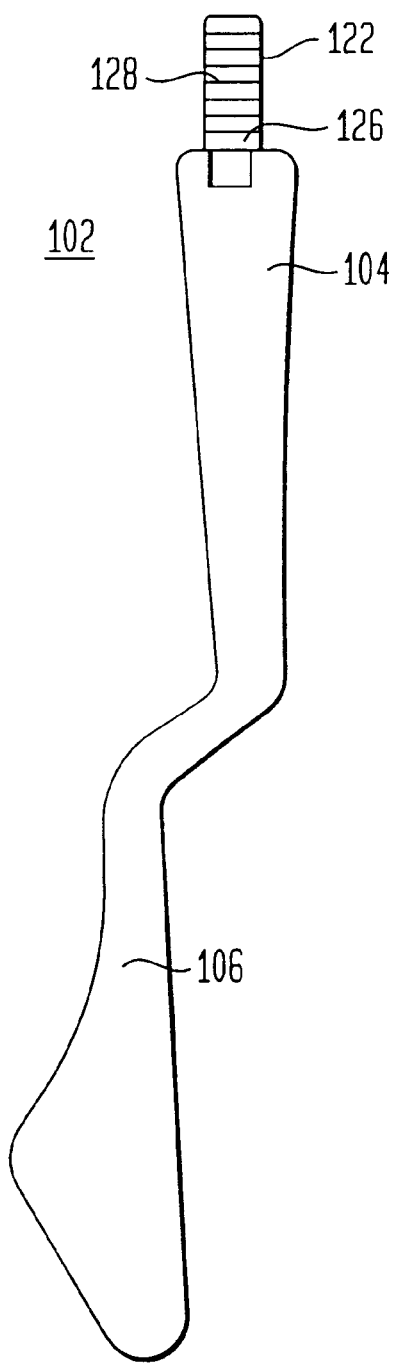
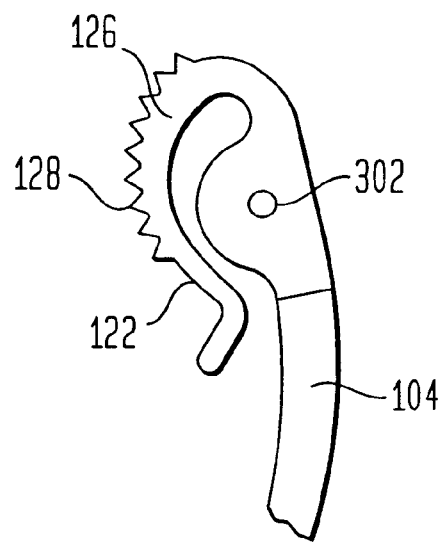

SPORTS TRAINING EYEGLASSES

CROSS REFERENCE TO RELATED APPLICATIONS

This application claims the benefit of application Ser. No. 60/142,357, filed in the U.S.P.T.O. on Jul. 6, 1999.

BACKGROUND OF INVENTION

1. Field of the Invention

This application relates to eyeglasses, and more particularly, to sports training eyeglasses having adjustable temporal side members, a movable nose piece, and opaque lenses, one pair of lenses having an elongated slit viewing aperture that is rotatably adjustable between a horizontal orientation and a vertical orientation.

2. Related Art

Eye-hand coordination is an essential element in nearly every sport. Indeed, sports such as baseball, golf or hockey require that a participant receive information with his eyes, process that information, form a course of action, and then transmit that course of action to the muscles in the body to carry out that action. Every step must take place in order for a participant to correctly hit a baseball, drive a golf ball, or slap a puck with the proper eye-hand coordination.

All of the steps in achieving proper eye-hand coordination require a precise and complex series of stimuli, processing, nerve reflexes, and muscle memory. In addition, exercising all of the steps of proper eye-hand coordination must often take place in an instant. As such, the seemingly simple task of driving a golf ball down a fairway is, in reality, a very complex biological process.

Of course the process can be improved and streamlined with practice and training. Nevertheless, a participant in a sport can spend countless hours trying to develop the correct eye-hand coordination. Those who are not initiated into a sport may spend even more hours trying to develop the correct eye-hand coordination, often to the point of frustration. In fact, those who wish to develop correct eye-hand coordination begin training at very early ages, improving reception of stimuli, processing what course of action to take, transmitting that action to the muscles, and having the muscles effect the correct action. Becoming proficient at even one step in the process may take years.

Therefore, there is a need for a training device that assists a user to "keep the eye on the ball." There is a further need for a training device that is adjustable such that the device can be customized for the user.

One obvious problem associated with training a user to "keep the eye on the ball" is the numerous distractions to the user that interfere with the user's ability to focus solely on the ball. Such distractions are often due to peripheral objects and/or lighting.

To address this problem, a pair of sports training eyeglasses are commercially available under U.S. Pat. No. 5,675,398 having opaque lenses with a small aperture centrally located. In operation, a user focuses on a ball through the aperture wherein all peripheral objects and lighting are removed from the user's sight. The disadvantages with the conventional sports training eyeglasses are that the eyeglasses cannot be custom fit to the user's head and the lenses may be easily knocked out of position. In addition, the lenses of the prior art eyeglasses can only be used with a moving ball, e.g., in softball and baseball. The prior art eyeglasses and lenses cannot be used with a stationary ball, e.g., in golf, because the lenses' apertures are too small and fixed in position such that they prevent the user from following through on his/her swing when hitting the stationary ball.

Therefore, there is a need for a pair of sports training eyeglasses that provides for accurate adjustment of the positions of the lenses to correspond to the pupillary position of a user while allowing the user to maintain eye contact with a stationary ball put into motion.

SUMMARY OF INVENTION

The present invention solves the problems associated with a user training to hit a ball by providing a pair of sports training eyeglasses comprising: (a) a pair of lenses, each lens comprising: (i) an opaque peripheral region, and (ii) a viewing aperture; and (b) a frame, comprising: (i) an elongated bridge bar having opposite ends, (ii) a pair of opposing temporal side members extending from respective ends of the elongated bridge bar, (iii) a means for adjusting the position of each temporal side member in relation to the elongated bridge bar, (iv) a movable nose piece, (v) a means for removably attaching each lens to the elongated bridge bar, wherein the position of the lens are adjustable in relation to the movable nose piece, and (vi) a means for securing, or locking, the position of the lens on the elongated bridge bar.

There are several advantages of the sports training eyeglasses of the present invention over the prior art. First, the temporal side members are not straight elongated side members, but now comprise a raised portion and a lower portion. This new design provides the means for the eyeglasses to be properly positioned on a user, as well as provides a more comfortable and secure fit. Second, the temporal side members are adjustably connected to the elongated bridge bar, thereby allowing a user to change the angle of each temporal side member in relation to the elongated bridge bar. This provides the user with a properly positioned, comfortable and secure fit of the eyeglasses. Third, the nose piece is movable and can be adjustably positioned so as to also provide a means for lowering or raising the sports training eyeglasses on the user's face. Fourth, the present sports training eyeglasses can easily be worn over conventional eyeglasses used to correct the user's vision.

Additional advantages pertain to the lenses of the present invention. The pair of lenses are removably attached to the elongated bridge bar, thereby allowing a user to switch between different types of lenses depending on the desired training. Further, the position of the lenses is slidably adjustable along the elongated bridge bar, thereby allowing the user to position the lenses in alignment with his/her pupils. Once the lenses are properly positioned, an elongated locking bar is used to secure the position of the lenses within the elongated bridge bar. The locking bar ensures that the lenses will not be accidently moved from their proper position.

There are also two different types of lenses that are used with the present invention. A first type of lens is disclosed for training players in ball related sports that require batting or hitting of a moving ball, e.g., baseball and softball. This lens has an opaque periphery and has a viewing aperture that is preferably oval in shape. A second type of lens is disclosed for training players in ball related sports that require hitting a stationary object, e.g., golf and hockey. This lens also has an opaque periphery, but has a viewing aperture that is an elongated slit. Also, the viewing aperture is located within a rotating member such that the viewing aperture is rotatably positionable within the lens, whereby the user can rotate the viewing aperture between a vertical orientation and a horizontal orientation. This rotation of the viewing aperture allows the user to custom fit the lenses within the elongated bridge bar and then, without moving the lenses' position but moving only the viewing aperture orientation, allows the user to train with the sports training eyeglasses.

BRIEF DESCRIPTION OF THE FIGURES

The present invention is described with reference to the accompanying drawings. In the drawings, like reference numbers indicate identical or functionally similar elements. Additionally, the left-most digit(s) of a reference number identifies the drawing in which the reference number first appears.

FIG. 2 is a planar side view of a temporal side member;

FIG. 3 is a planar side view of an engaging member of the temporal side member;

DETAILED DESCRIPTION OF THE PREFERRED EMBODIMENTS

Figure 1:
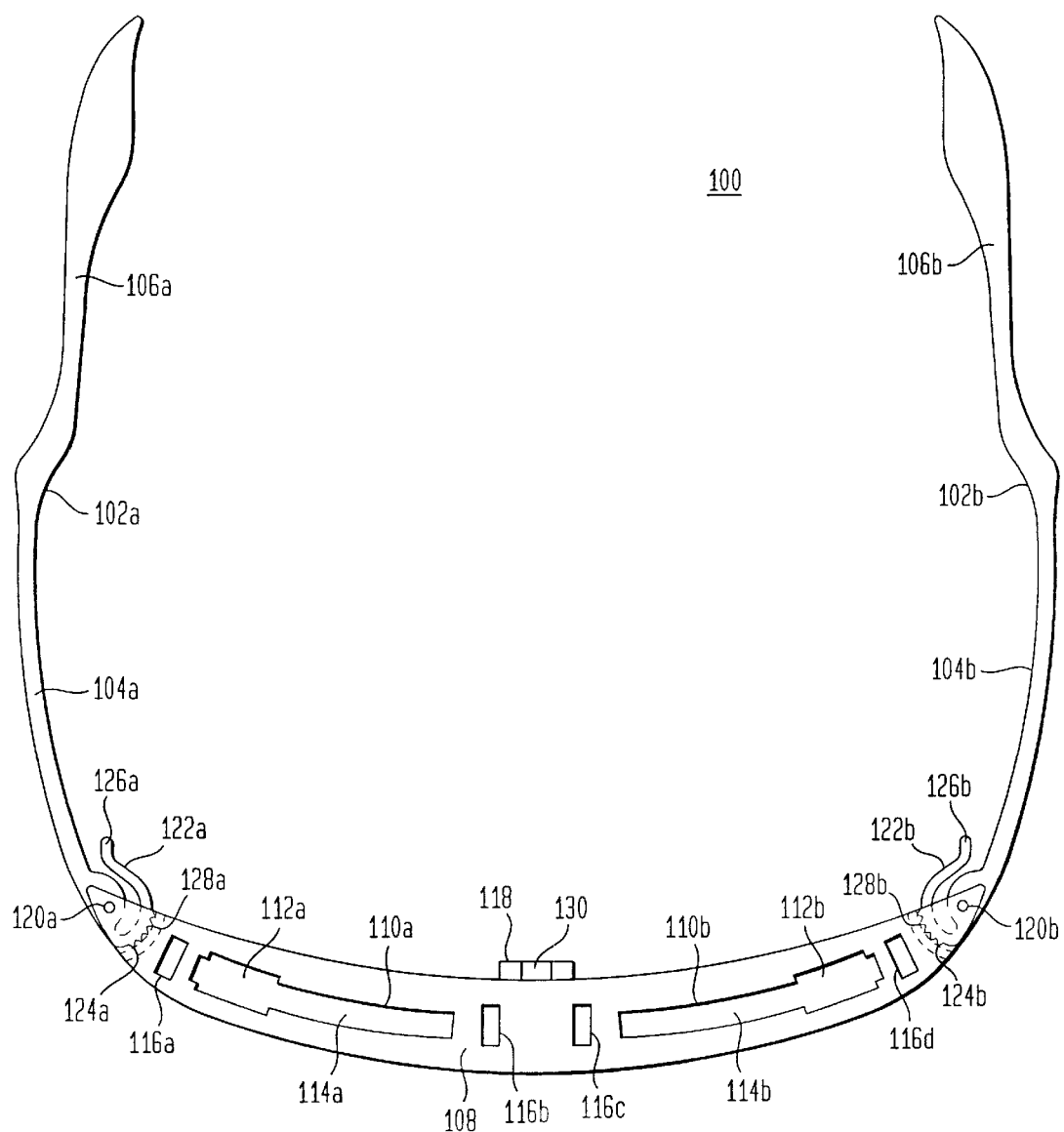
FIG. 1 is a planar top view of a preferred embodiment of a pair of sports training eyeglasses of the present invention.

Referring now to the drawings in detail and initially to FIG. 1, the preferred embodiment of a pair of sports training eyeglasses of the present invention comprises an elongated bridge bar 108 having opposite ends with a temporal side member 102a,b attached to each end, a movable nose piece 118, a pair of lens receiving channels 110a,b (comprising a lens insertion portion 112a,b and a lens holding portion 114a,b), and a means for dynamically adjusting and locking the temporal side members 102a,b in relation to the elongated bridge bar 108.

In the preferred embodiment, the means for dynamically adjusting and locking the temporal side members 102a,b comprises a temporal side member 102a,b being pivotally connected to the elongated bridge bar 108 via a pin 120a,b. Further, a first engaging member 122a,b is integrally connected to a temporal side member 102a,b and a second engaging member 124a,b is integrally connected to the elongated bridge bar 108 such that the first engaging member 122a,b dynamically engages and disengages the second engaging member 124a,b.

In the preferred embodiment, the first engaging member 122a,b is a flexible flange 126a,b having a plurality of saw-tooth ridges 128a,b positioned on the flange's 126a,b exterior surface. The second engaging member 124a,b is also a plurality of saw-tooth ridges and is positioned on an internal surface of the elongated bridge bar 108. In operation, the user simply pulls back on the flange 126a,b of the first engaging member 122a,b to disengage the saw-tooth ridges 128a,b of the first engaging member 112a,b from the saw-tooth ridges of the second engaging member 124a,b and then positions the temporal side member 102a,b to a comfortable angle. Once the proper angle is determined, the user releases the flange 126a,b of the first engaging member 122a,b, thereby allowing the saw-tooth ridges 128a,b of the flange 126a,b to engage the saw-tooth ridges of the second engaging member 124a,b and hold the temporal side member 102a,b in the selected position. The means for adjusting the temporal side members 102a,b is described in these terms for convenience purpose only. It would be readily apparent for one of ordinary skill in the relevant art(s) to use a comparable means for adjusting the temporal side members 102a,b for a user.

The sports training eyeglasses 100 of the present invention can also be adjusted for a comfortable and proper fit on a user by moving the nose piece 118 about a pivot point 130. A user rotates the nose piece 118 up to lower the sports training eyeglasses 100 on his/her face and rotates the nose piece 118 down to raise the sports training eyeglasses 100 on his/her face.

FIG. 2 is a planar side view of a temporal side member 102 showing a raised portion 104 and a lower portion 106 in order to provide a more ergonomic fit for a user. It would be readily apparent for one of ordinary skill in the relevant art(s) to use a different design and shape for a temporal side member 102a,b.

The first engaging member 122 of a temporal side member 102 is shown in detail in FIG. 3 wherein the flange 126 of the first engaging member 122 has the saw-tooth ridges 128 on its external edge. Further, an aperture 302 is located in the first engaging member 122 for receiving a pin 120, thereby allowing the user to adjust, or pivot, the temporal side member 102 in relation to the elongated bridge bar 108.

Figure 4:
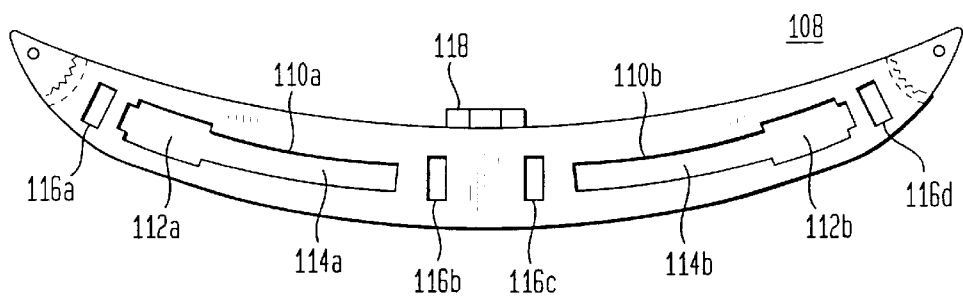
FIG. 4 is a planar top view of an elongated bridge bar.
Figure 5:
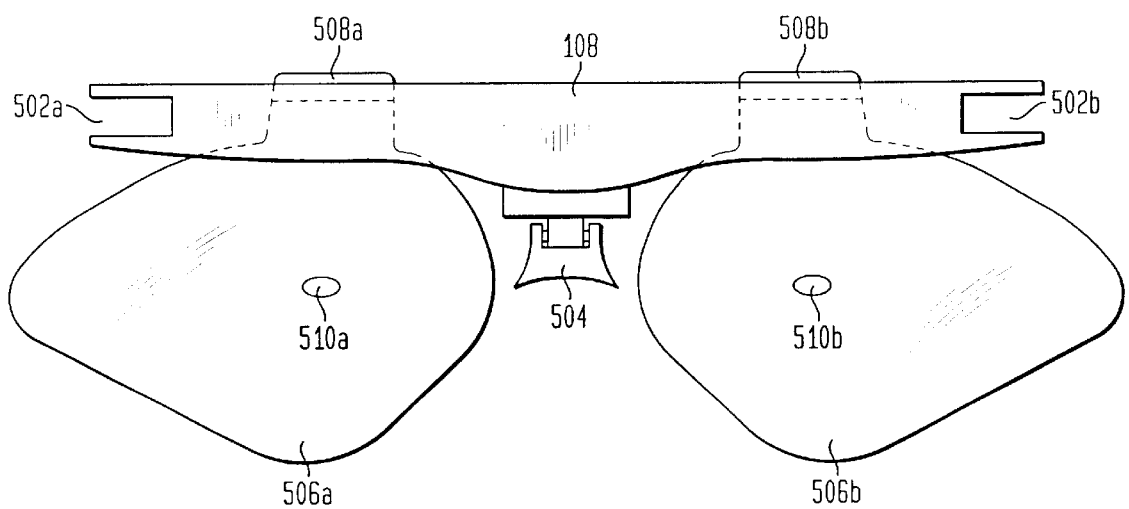
FIG. 5 is a planar front view of the elongated bridge bar 108 of the present invention with a pair of lenses.

Another aspect of the sport training eyeglasses 100 of the present invention is an elongated bridge bar 108 of the present invention used to install and hold a pair of lenses in place. FIG. 4 shows a top view of the elongated bridge bar 108, wherein FIG. 5 shows the sports training eyeglasses 100 with a pair of lenses 506a,b attached thereto by a means for removably attaching the lenses 506a,b to the elongated bridge bar 108.

In the preferred embodiment, the means for removably attaching a lens 506a,b to the elongated bridge bar 108 comprises a channel engaging member 508a,b integrally attached to the top of each lens 506a,b and a pair of lens receiving channels 110a,b extending through the elongated bridge bar 108 from top to bottom. In operation, a lens 506a,b is attached to the elongated bridge bar 108 by inserting the channel engaging member 508a,b of each lens 506a,b through a lens insertion portion 112a,b of each lens receiving channel 110a,b in the elongated bridge bar 108. Then, the user slides the lens' 506a,b channel engaging member 508a,b into a lens holding portion 114a,b until the desired position is found. Once the lenses 506a,b are installed in the lens holding portion 114a,b of the elongated bar 108, the user positions them such that a viewing aperture 510a,b of each lens 506a,b is aligned with his/her pupils. The method for adjusting, or properly fitting, the lens 506a,b of the sports training eyeglasses 100 of the present invention is described in greater detail below.

In a lens receiving channel 110a,b, the lens insertion portion 112a is wider than the lens holding portion 114a,b. Thus, the channel engaging member 508 of each lens 506a,b can fit through the wider lens insertion portion 112a,b. When slid into the narrower lens holding portion 114a,b, the channel engaging member 508a,b is held in place. The channel engaging member 508a,b is described in greater detail below.

Figure 6:
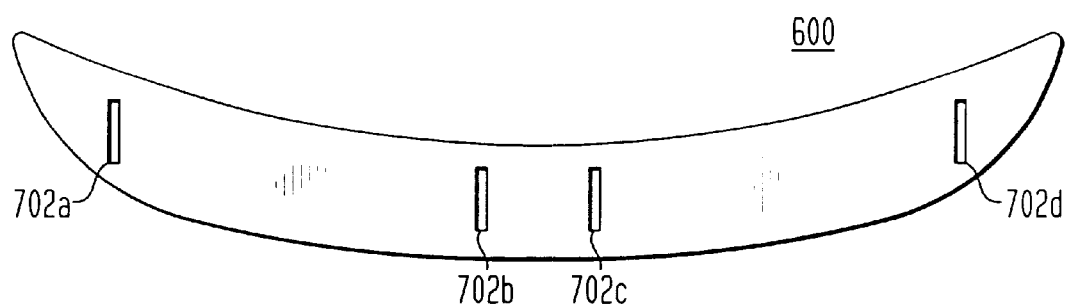
FIG. 6 is a planar top view of an elongated locking bar.
Figure 7:
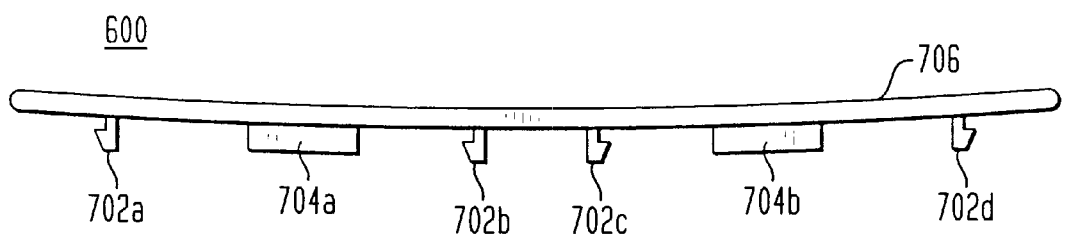
FIG. 7 is a planar side view of the elongated locking bar.

Once the lenses 506a,b are in the proper position within the elongated bridge bar 108, an elongated locking bar 600 is "snapped-onto" the top of the elongated bridge bar 108. FIG. 6 shows a top view of the elongated locking bar 600 while FIG. 7 shows a side view. Once secured, or locked, the elongated locking bar 600 prevents the lenses 506a,b from moving out of position. As illustrated, the preferred embodiment of the elongated locking bar 600 comprises the same general shape and dimensions as the top view of the elongated bridge bar 108. However, this is for convenience only. It would be readily apparent to one of ordinary skill in the relevant art(s) to use a comparable means for locking the lenses 506a,b to the elongated bridge bar 108, e.g., a one or more clips, fasteners, etc.

In the preferred embodiment, the elongated locking bar 600 comprises a means for attaching to the elongated bridge bar 108 and a means for locking the position of the lenses 506a,b in the lens receiving channel 110a,b of the elongated bridge bar 108. The means for attaching to the elongated bridge bar 108 is a plurality of locking flanges 702a–d that are inserted into apertures 116a–d and through the top of the elongated bridge bar 108, wherein once the locking flanges 702a–d are inserted in the apertures 116a–d and the elongated locking bar 600 is rigidly attached to the top of the elongated bridge bar 108.

The means for locking the lenses 506a,b comprises a pair of locking protrusions 704a,b extending downward from the bottom of the elongated locking bar 600. In operation, when the elongated locking bar 600 is "snapped" into the elongated bridge bar 108, the locking protrusions 704a,b are aligned with and inserted into the top of the channel engaging member 508a,b of each lens 506a,b, resulting in the lenses 506a,b being locked in position in relation to the nose piece 118. The channel engaging member 508a,b of the lenses 506a,b are described in greater detail below.

Figure 8:
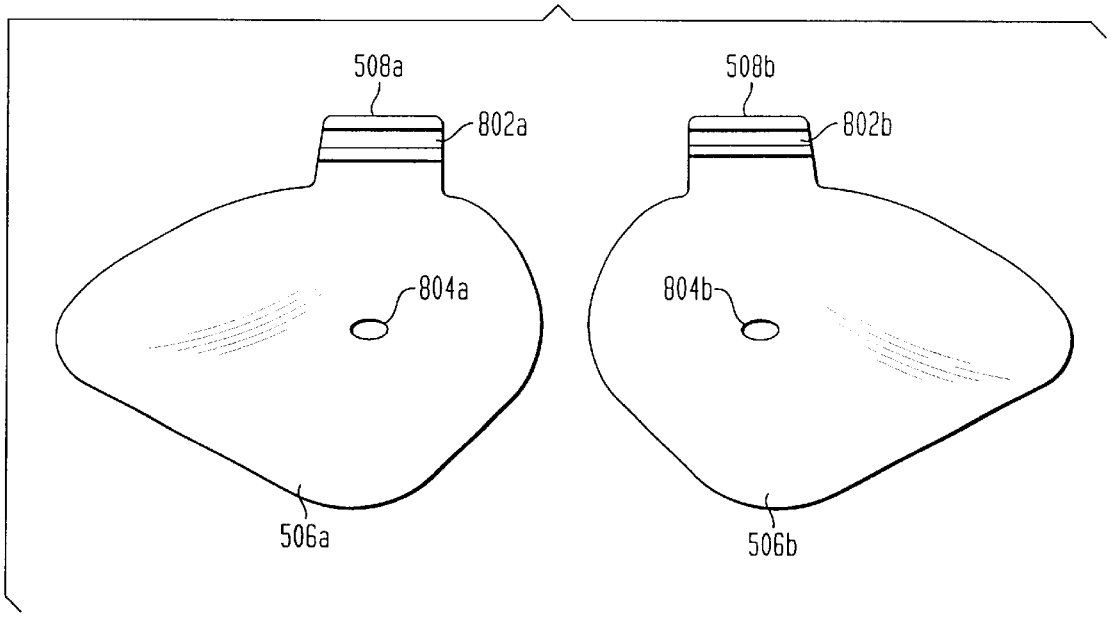
FIG. 8 is a planar front view of a first pair of lenses for training a person to hit a moving ball.
Figure 9:
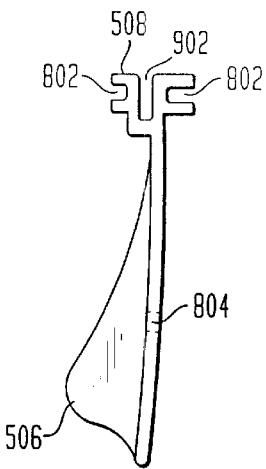
FIG. 9 is a planar side view of the first pair of lenses.
Figure 10:
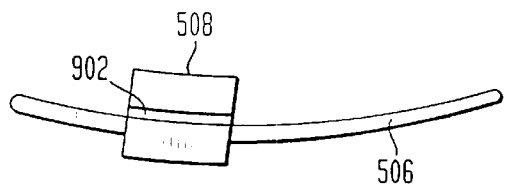
FIG. 10 is a planar top view of the first pair of lenses.

The present invention has two different types of lenses. The first pair of lenses 506a,b are for training a user to hit a moving ball, such as hitting a baseball or softball with a bat, and are shown in FIGS. 8–10. Each lens 506a,b is opaque, has an oval shaped viewing aperture 804a,b and has a channel engaging member 508a,b. The shape of the viewing aperture 804a,b is for convenience purpose only. It would be readily apparent for one of ordinary skill in the relevant art to use a different shaped viewing aperture 804a,b. In operation, the two sides of a lens receiving channel 110a,b of the elongated bridge bar 108 slides through a channel receiving portion 802a,b of the channel engaging member 508a,b, resulting in the lens 506a,b being suspended down from the elongated bridge bar 108.

The locking receiver cavity 902 of a lens 506a,b receives and holds a locking protrusion 704a,b of an elongated locking bar 600. Therefore, when an elongated locking bar 600 is attached to an elongated bridge bar 108 having a lens 506a,b in the lens receiving channel 110a,b, the locking protrusions 704a,b of the elongated locking bar 600 align with and engage the locking receiver cavity 902 of the lens' 506a,b channel engaging member 508a,b, resulting in the lens 506a,b being securely held in position.

Figure 11:
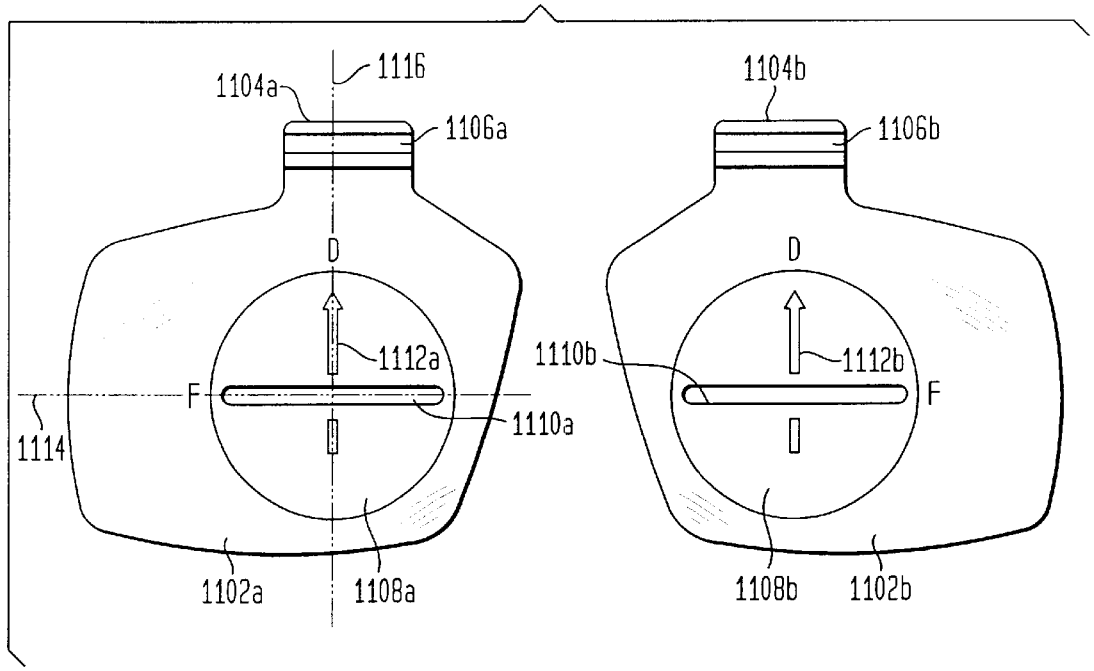
FIG. 11 is a planar front view of a second pair of lenses for training a person to hit a stationary ball.
Figure 12:
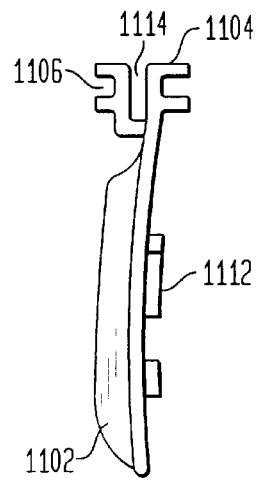
FIG. 12 is a planar side view of the second pair of lenses.
Figure 13:
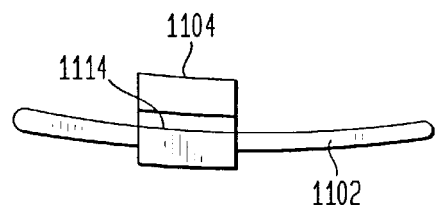
FIG. 13 is a planar top view of the second pair of lenses.
Figure 14:
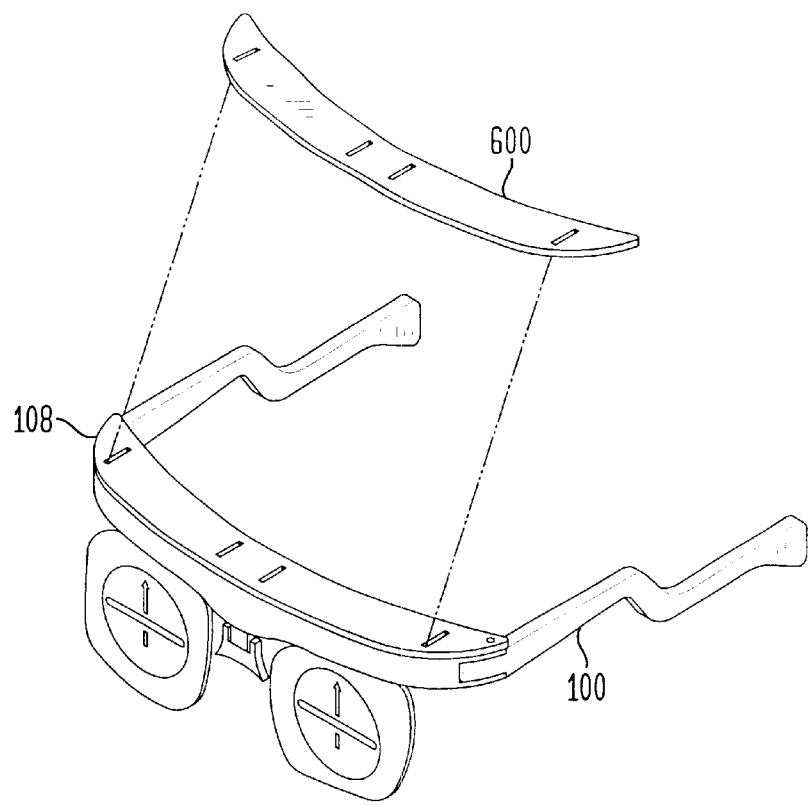
FIG. 14 is a perspective view of the sports training eyeglasses with the elongated locking bar.
Figure 15:
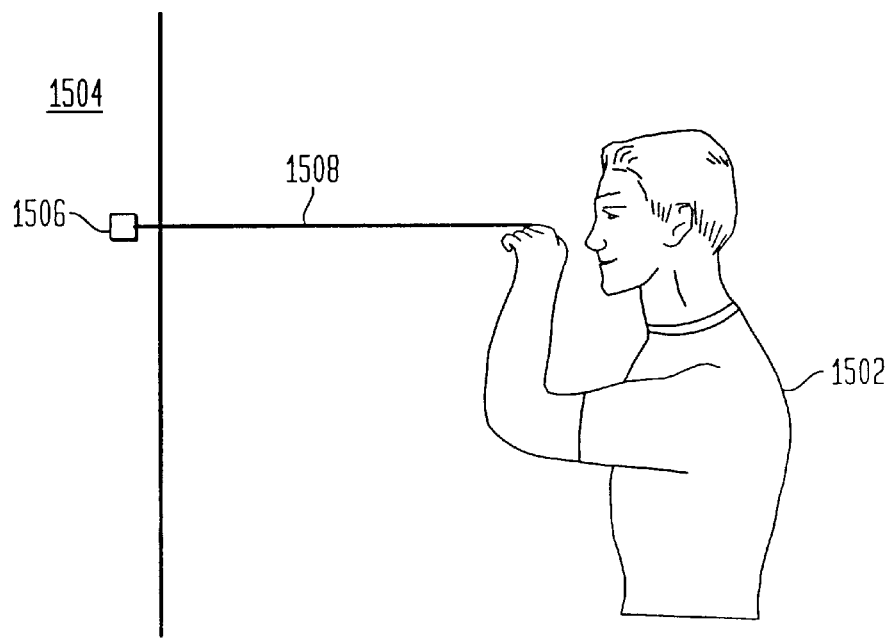
FIG. 15 is a perspective view of a user setting up a target for fitting the sports training eyeglasses.
Figure 16:
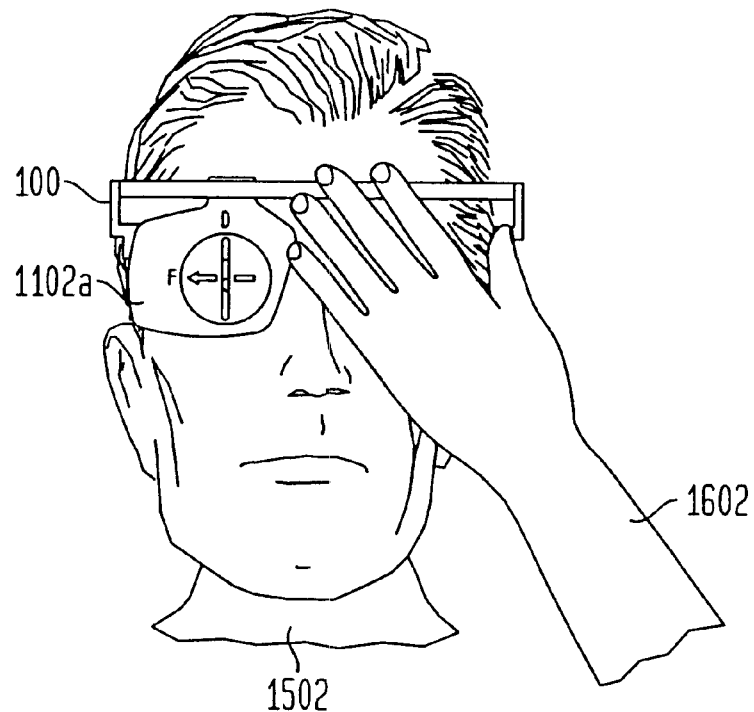
FIG. 16 is a perspective view of a user customizing the lenses of the sports training eyeglasses.
Figure 17:
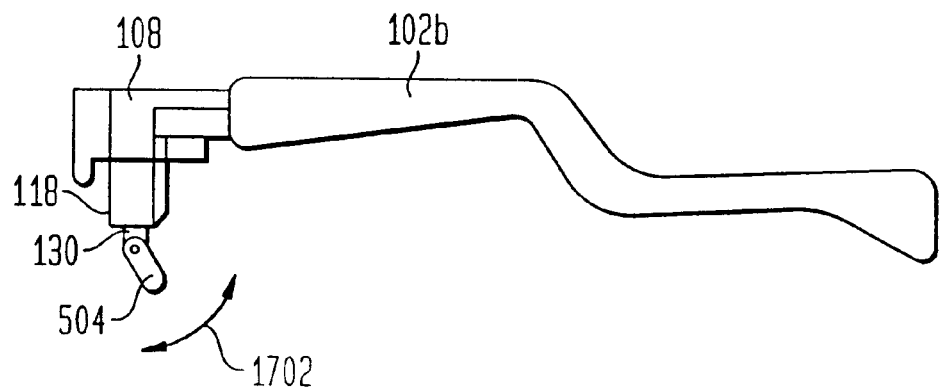
FIG. 17 is a planar side view of adjusting a nose piece of the sports training eyeglasses.
Figure 18:
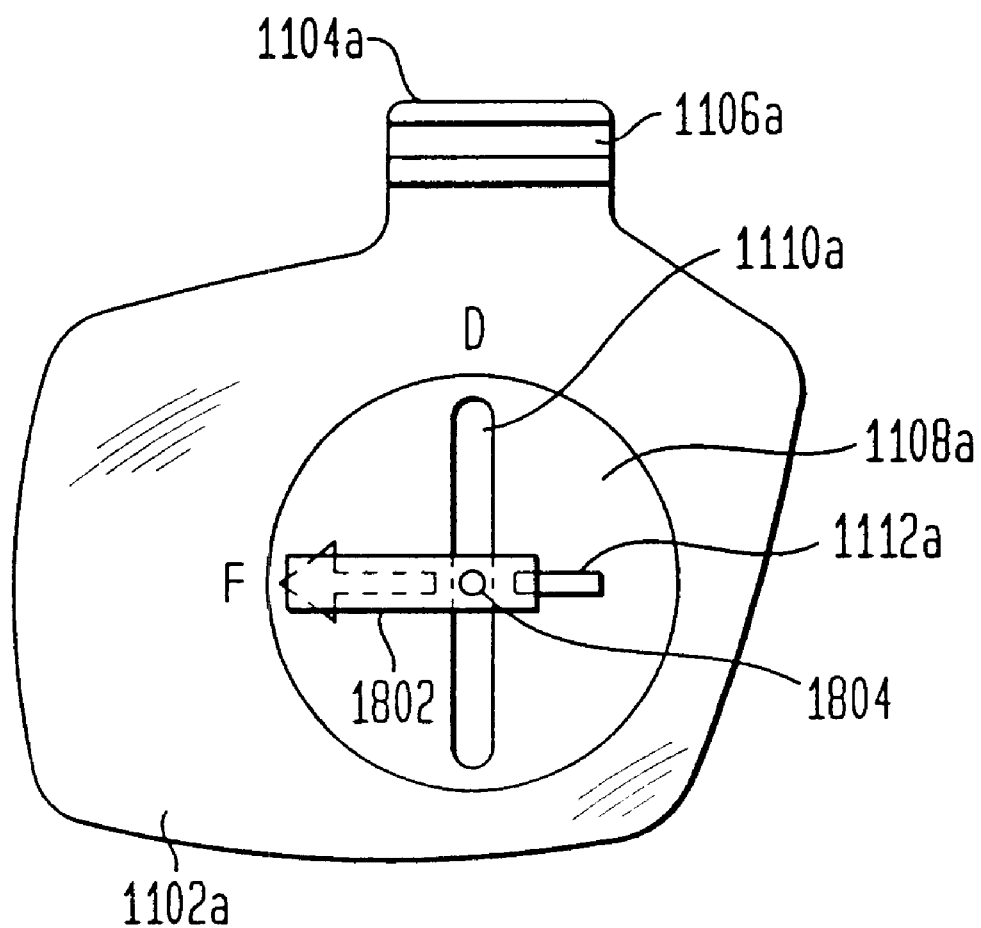
FIG. 18 is a planar front view of the second pair of lenses for training a person to hit a stationary golf ball having a removable lens cover.

The second pair of lenses 1102a,b of the present invention are for training a person to hit a stationary ball, e.g., golf, and are shown in FIGS. 11–13. Each lens 1102a,b is opaque, has a rotating member 1108a,b with an elongated slit viewing aperture 1110a,b and has a channel engaging member 1104a, b. A rotating member 1108a,b of a lens 1102a,b provides the means for the user to rotate the viewing aperture 1110a,b between a horizontal orientation and a vertical orientation. The user simply holds the rotating member 1108a,b and turns it until the viewing aperture 1110a,b is in the desired orientation.

In the preferred embodiment, each lens 1102a,b has a "F" designation on a horizontal axis 1114 of the lens 1102a,b, and a "D" designation on a vertical axis 1116 of the lens 1102a,b. The "F" designation means "Fitting" and is used to indicate to the user that the viewing aperture 1110a,b should be rotated to the vertical position when fitting the user with the correct position of the lenses 1102a,b. This is facilitated by the use of a operational indicator 1112a,b incorporated onto the rotating member 1108a,b, which in the preferred embodiment is an arrow. Therefore, when a user is to be "fitted" with the eyeglasses, the operational indicator 1112a,b is rotated to the "F" designation, resulting in the viewing aperture 1110a,b being placed in the required vertical orientation. The "D" designation means "Driving" and is used when training a user to hit a stationary ball, e.g., training the user's golf swing. When the operational indicator 1112a,b is pointing to the "D" designation, the viewing aperture 1110a,b is in the horizontal orientation which allows the user to have lateral head movement while preventing any up/down movement of the head. This allows the user to be better balanced when hitting, thereby achieving better results.

The lenses 1102a,b described herein for training a user to hit a stationary ball is attached to an elongated bridge bar 108 of the sports training eyeglasses 100 of the present invention in the same manner as the lenses 506a,b used for training a user to hit a moving ball. Specifically, a channel receiving portion 1106a,b of the channel engaging member 1104a,b, of the lenses 1102a,b slides between and through the sides of a lens receiving channel 110a,b of the elongated bridge bar 108 of the sports training eyeglasses 100, resulting in the lenses 1102a,b being suspended down from the bottom of the elongated bridge bar 108.

The locking receiver cavity 1114 receives and holds a locking protrusion 704a,b of an elongated locking bar 600. Therefore, when an elongated locking bar 600 is attached to an elongated bridge bar 108 having a lens 1102a,b in the lens receiving channel 110a,b, the locking protrusions 704a,b of the elongated locking bar 600 engage the locking receiver cavity 1114 of the lens' 1102a,b channel engaging member 1104a,b, resulting in the lens 1102a,b being securely held in position.

In the preferred embodiment, the sports training eyeglasses 100 and lenses 506a,b, 1102a,b of the present invention are made of a composite material, e.g., a hard plastic. However, they can be made of any comparable material. In addition, the present invention has the following preferred measurements: elongated bridge bar 108 has a length of 5¾" and a width of ½"; temporal side member 102 has a length of 6¾"; lens receiving channel 110 has a length of 1¾"; nose piece 118 drops down ⅞" from the bottom of the elongated bridge bar 108; the first pair of lenses 506 for hitting a moving ball have a length of 3", a width of 1⅞", a viewing aperture 804 length of ⅜", a viewing aperture 804 width of ¼", and a channel engaging member 508 width of ⅝"; and the second pair of lenses 1102 for hitting a stationary ball have a length of 2½", a width of 2¼", an elongated slit viewing aperture 1110 length of 1⅜", an elongated slit viewing aperture 1110 width of ⅛", and a channel engaging member 1104 width of ⅝".

These measurements are used for convenience purpose only to illustrate an adult size pair of sports training glasses 100. It would be readily apparent for one of ordinary skill in the relevant art to use comparable measurements or scale the sports training glasses 100 for a different size pair of eyeglasses, e.g., junior size sports training eyeglasses 100.

In addition, the preferred embodiment of the lenses 506*a, b*, 1102*a,b* of the sports training eyeglasses 100 of the present invention are black in order to enhance the effectiveness of the sports training eyeglasses. That is, the more opaque the periphery of the lenses 506*a,b*, 1102*a,b* are, the better a user is able to focus on his/her training and the hitting of a ball. The use of black is for convenience purpose only. It would be readily apparent to one of ordinary skill in the relevant art to use a comparable means for making the lenses 506*a,b*, 1102*a,b* opaque.

Before a user begins to train with the sports training eyeglasses 100 of the present invention for training to hit a ball, the user must customize the sports training eyeglasses 100 to ensure that it properly fits his/her face. FIGS. 14–18 illustrate the preferred method for customizing the sports training eyeglasses 100 using the second pair of lenses 1102*a,b*. The method for customizing is described in terms of the second pair of lenses 1102*a,b* for convenience purpose only. It would be readily apparent to one of ordinary skill in the relevant art to customize the sports training eyeglasses 100 of the present invention using either the first set of lenses 506*a,b*, or any other lenses that are designed to work with the sports training eyeglasses 100.

First, the user 1502 must set up the lens calibration target 1506. The user 1502 attaches the lens calibration target 1506 to a flat surface, e.g., a wall, at eye level and then marks off a distance of approximately ten (10) feet from the lens calibration target 1506. In the preferred embodiment, a string 1508 having a length of about ten (10) feet is attached to the lens calibration target 1506 such that the user 1502 simply has to hold the string 1508 and back away from the lens calibration target 1506 the full length of the string 1508. The user 1502 marks the spot, e.g., with a coin or golf tee, on the floor corresponding to the length of ten (10) feet from the lens calibration target 1506.

After the lens calibration target 1506 is properly set up, the user 1502 is ready to adjust the position of the lenses 1102*a,b* within the sports training eyeglasses 100 for a proper fit. The following description of adjusting the proper fit of a lens 1102*a,b* with the sports training eyeglasses 100 is described in reference to a single lens 1102*a* for convenience purpose only. The method of adjusting the first lens 1102*a* is equally applicable for adjusting the proper position of the second lens 1102*b* within the sports training eyeglasses 100.

First, the user 1502 inserts the lens' 1102*a* channel engaging member 1104*a* through the lens insertion portion 112*a* of the lens receiving channel 110*a* of the elongated bridge bar 108. Then, the user slides the lens' 1102*a* channel engaging member 1106*a* into and through the lens holding portion 114*a* just far enough so the lens 1102*a* does not fall out of the lens receiving channel 110*a*. This is repeated for both lenses 1102*a,b*. Once the lenses 1102*a,b* are positioned in the elongated bridge bar 108, the user gently places the elongated locking bar 600 on top of the elongated bridge bar 108 without actually pressing down or locking the elongated locking bar 600 to the elongated bridge bar 108. See FIG. 14.

Once the lenses 1102*a,b* are installed on the sports training eyeglasses 100, the user 1502 must customize the position of the lenses 1102*a,b* to the actual distance between his/her pupils. The user 1502 puts the sports training eyeglasses 100 on. If the sports training eyeglasses 100 are too tight or uncomfortable, the user 1502 must adjust the angle of the temporal side members 102*a,b*. To do this, using one temporal side member 102*a* as an example, the user 1502 simply pulls back on the flange 126*a* of the first engaging member 122*a* to disengage the first engaging member 112*a* from the second engaging member 124*a*. The user 1502 then positions the temporal side member 102*a* to a comfortable angle. Once the proper angle is determined, the user 1502 releases the flange 126*a* of the first engaging member 122*a*, thereby allowing the saw-tooth ridges 128*a* of the flange 126*a* to engage the saw-tooth ridges of the second engaging member 124*a* and hold the temporal side member 102*a* in the selected position. In the preferred embodiment, once a comfortable fit is achieved, the user 1502 may remove the sports vision eyeglasses 100 and tightens the temporal side member 102*a* one more notch of the saw-tooth ridges 128*a* to assure a secure fit. The user 1502 should adjust both temporal side members 102*a,b* for a proper fit.

In the preferred embodiment of the present invention, each lens 1102*a* has a removable lens cover 1802 attached to the front of the lens 1102*a* wherein a pinhole aperture 1804 of the removable lens cover 1802 is aligned with the approximate center of the viewing aperture 1110*a* of the lens 1102*a*. In fitting the sports training eyeglasses 100, the user 1502 looks through the pinhole aperture 1804 to ensure proper pupil alignment of the lens 1102*a*. The method of using the removable lens cover 1802 is described in greater detail below.

Next, the user 1502 makes sure the operational indicators 1112*a,b* of the lenses 1102*a,b* are rotated to the "F" designation, indicating "Fitting," resulting in the elongated slit viewing aperture 1110*a,b* being placed in the required vertical orientation. Facing the lens calibration target 1506, the user 1502 covers a first eye, e.g., by closing the first eye or placing a hand 1602 over the first eye. The user 1502 then gently slides the lens 1102*a* over the second eye left or right in the lens holding portion 114*b* of the lens receiving channel 110*a* until the calibration target 1506 comes into view through the pinhole aperture 1804 of the removable lens cover 1802, which in the preferred embodiment is a sticker. This process is repeated for the second lens 1102*b* wherein the user 1502 covers a second eye and adjusts the position of the lens 1102*b* over the first eye. Once both lenses 1102*a,b* are properly positioned, the user 1502 snaps the elongated locking bar 600 into place, thereby locking and securing the lenses 1102*a,b* in position within the sports training eyeglasses 100. Once the lenses 1102*a,b* are properly positioned, the user 1502 removes the removable lens cover 1802 from both lenses 1102*a,b*.

If the user 1502 cannot see the calibration target 1506 through the pinhole aperture 1804 without moving his/her head up or down, the user 1502 must adjust the position of the sports training eyeglasses 100 via the movable nose piece 118. Specifically, the movable nose piece 118 rotates around pivot point 130, thereby having a range of motion equal to angle 1702. By moving the nose piece 118 around the angle 1702, the user 1502 moves the sports vision eyeglasses 100 up or down on his/her face. Specifically, by rotating the nose piece 118 up, the sports vision eyeglasses 100 sit lower on the user's 1502 face, and by rotating the nose piece 118 down, the sports vision eyeglasses 100 sit higher on the user's 1502 face. The movable nose piece 118 also allows the sports training eyeglasses 100 to be worn over conventional corrective eyeglasses.

Once the user 1502 has properly customized the sports training eyeglasses 100, the user 1502 removes the sports training eyeglasses 100 and rotates the operational indicators 1112*a,b* of the lenses 1102*a,b* to the "D" designation, indicating "Driving," resulting in the elongated slit viewing aperture 1110*a,b* being placed in the required horizontal orientation. Now the sports training eyeglasses 100 are ready for training the user 1502 to keep his/her eye on the ball.

As one example of training to hit a stationary ball, the user 1502 places a golf ball on a tee (or on the ground to practice other types of golf shots). Looking at the golf ball through the viewing apertures 1110*a,b*, the user 1502 keeps the golf ball in sight while practicing a specific golf swing. If the user 1502 loses sight of the golf ball, then the user 1502 sees only black. Therefore, the user 1502 adjusts the position of his/her swing and head so the golf ball stays in his/her field of vision throughout the entire swing. If the user 1502 has trouble completing a swing without losing sight of the golf ball, the user 1502 should make very slow and deliberate swings to ensure that the golf ball remains within view through the viewing apertures 1110*a,b*. The user 1502 should slowly increase the speed of his/her swing, until normal swing speed is reached, while concentrating on keeping it consistent as well as on keeping his/her eye on the golf ball.

The method for adjusting and training with the sports training eyeglasses 100 of the present invention described above can be used with the first set of lenses 506*a,b* for use with a moving ball. However, in this use, the lenses 506*a,b* do not have a rotatable viewing aperture 510*a,b*, so the user 1502 should omit those steps from the process.

CONCLUSION

While various embodiments of the present invention have been described above, it should be understood that they have been presented by the way of example only, and not limitation. It will be understood by those skilled in the art that various changes in form and details may be made therein without departing from the spirit and scope of the invention as defined in the specification and the appended claims. Thus, the breadth and scope of the present invention should not be limited by any of the above-described exemplary embodiments, but should be defined in accordance with the specification and any equivalents.

I claim:

1. A pair of eyeglasses, comprising:
    a. a pair of lenses, each lens comprising:
       (i) an opaque peripheral region, and
       (ii) a viewing aperture; and
    b. a frame, comprising:
       (i) an elongated bridge bar having opposite ends,
       (ii) a pair of opposing temporal side members extending from respective ends of said elongated bridge bar,
       (iii) a means for dynamically adjusting and locking a position of each said temporal side member in relation to said elongated bridge bar,
       (iv) a nose piece movably attached to an approximate center point of said elongated bridge bar,
       (v) a means for removably attaching each said lens to said elongated bridge bar, wherein the position of each said lens is adjustable in relation to said nose piece, and
       (vi) a means for locking the position of each said lens on said elongated bridge bar.

2. The pair of eyeglasses according to claim 1, wherein said temporal side members have a raised portion and a lower portion.

3. The pair of eyeglasses according to claim 1, wherein said viewing aperture of each said lens comprises an oval shape.

4. The pair of eyeglasses according to claim 3, wherein said viewing aperture of each said lens has a length of about $3/8$ inches and a width of about $1/4$ inches.

5. The pair of eyeglasses according to claim 1, wherein said viewing aperture of each said lens comprises an elongated slit.

6. The pair of eyeglasses according to claim 5, wherein said viewing aperture of each said lens has a length of about $1 3/8$ inches and a width of about $1/8$ inches.

7. The pair of eyeglasses according to claim 5, wherein said viewing aperture of each said lens is rotatably positionable in said lens, wherein said view aperture can rotate between a horizontal orientation and a vertical orientation.

8. The pair of eyeglasses according to claim 7, wherein said viewing aperture is in said vertical orientation for fitting the pair of eyeglasses and said viewing aperture is in said horizontal orientation for training with the pair of eyeglasses.

9. The pair of eyeglasses according to claim 7, wherein each said lens further comprises a means for indicating said horizontal orientation and said vertical orientation of said viewing aperture.

10. The pair of eyeglasses according to claim 9, wherein said means for indicating said horizontal orientation and said vertical orientation of said viewing aperture of each said lens comprises a "F" designation at a fixed location on a horizontal axis of said lens, a "D" designation at a fixed location on a vertical axis of said lens, and an operational indicator that is rotatably adjustable with said viewing aperture, wherein when said operational indicator points to said "F" designation, said viewing aperture is in said vertical orientation, and when said operational indicator points to said "D" designation, said viewing aperture is in said horizontal orientation.

11. The pair of eyeglasses according to claim 10, wherein said operational indicator of each said lens is an arrow.

12. The pair of eyeglasses according to claim 1, wherein said means for removably attaching each said lens comprises a lens receiving channel in said elongated bridge bar and a channel engaging member attached to each said lens, wherein said channel engaging member of each said lens slides within said lens receiving channel of said elongated bridge bar to position said lens in relation to said nose piece.

13. The pair of eyeglasses according to claim 12, wherein said means for locking the position of each said lens comprises an elongated locking bar having a means for attaching said elongated locking bar to said elongated bridge bar and a means for locking said channel engaging member of each said lens in said lens receiving channel of said elongated bridge bar.

14. The pair of eyeglasses according to claim 1, wherein said pair of lenses and said frame are black.

15. The pair of eyeglasses according to claim 1, wherein said means for dynamically adjusting and locking a position of each said temporal side member in relation to said elongated bridge bar comprises a first engaging member integrally connected to each said temporal side member and a second engaging member integrally connected to each side of said elongated bridge bar such that one said first engaging member dynamically engages and disengages one said second engaging member.

16. The pair of eyeglasses according to claim 15, wherein said first engaging member is a flexible flange having a plurality of saw-tooth ridges positioned on an exterior surface of said flange and said second engaging member is positioned on an internal surface of said elongated bridge bar and has is a plurality of saw-tooth ridges.

17. The pair of eyeglasses according to claim 1, wherein each said temporal side member is pivotally connected to an end of said elongated bridge bar by a pin.

18. The pair of eyeglasses according to claim 1, wherein said nose piece is rotatably adjustable in relation to said elongated bridge bar.

19. The pair of eyeglasses according to claim 1, wherein each said lens further comprises a removable cover element having a pinhole aperture that overlays said viewing aperture of said viewing lens.

20. A method for training a user to hit a stationary ball, said method comprising the steps:
(a) adjusting a pair of eyeglasses as claimed in claim 5 wherein said elongated slit of each said lens is in said vertical orientation;
(b) wearing said pair of eyeglasses;
(c) standing about ten feet away from a lens calibration target;
(d) adjusting the position of said lenses to correspond to the user's pupils;
(e) adjusting said elongated slit of each said lens to said horizontal position; and
(f) hitting the stationary ball while wearing said pair of eyeglasses.

21. The method according to claim 20, further comprising the steps of:
(g) adjusting each said temporal side member in relation to said elongated bridge bar to a comfortable position on the user; and
(h) locking the position of each said temporal side member.

22. The method according to claim 20, further comprising the step of:
(g) rotatably adjusting said nose piece in relation to said elongated bridge bar to a comfortable position on the user.

23. The method according to claim 20, further comprising the step of:
(g) locking the position of said lenses in said elongated bridge bar.

24. The method according to claim 20, wherein each said lens further comprises a removable cover element having a pinhole aperture that overlays said viewing aperture of said lens, said step (d) comprising the steps of:
(d.1) covering a first eye of the user;
(d.2) sliding said lens over the second eye of the user until said lens calibration target is in view through said pinhole aperture overlaying said viewing aperture;
(d.3) uncovering the first eye of the user;
(d.4) covering the second eye of the user;
(d.5) sliding said lens over the first eye of the user until said lens calibration target is in view through said pinhole aperture overlaying said viewing aperture;
(d.6) uncovering the second eye of the user; and
(d.7) removing said cover element from each said lens.

25. A method for training a user to hit a moving ball, said method comprising the steps:
(a) adjusting a pair of eyeglasses as claimed in claim 3, wherein each said temporal side member in relation to said elongated bridge bar is a comfortable position on the user;
(b) locking the position of each said temporal side member;
(c) rotatably adjusting said nose piece in relation to said elongated bridge bar to a comfortable position on the user;
(d) wearing said pair of eyeglasses;
(e) standing about ten feet away from a lens calibration target;
(f) adjusting the position of said lenses to correspond to the user's pupils;
(g) locking the position of said lenses in said elongated bridge bar; and
(h) hitting at the moving ball while wearing said pair of eyeglasses.

26. The method according to claim 25, wherein each said lens further comprises a removable cover element having a pinhole aperture that overlays said viewing aperture of said lens, said step (f) comprising the steps of:
(f.1) covering a first eye of the user;
(f.2) sliding said lens over the second eye of the user until said lens calibration target is in view through said pinhole aperture overlaying said viewing aperture;
(f.3) uncovering the first eye of the user;
(f.4) covering the second eye of the user;
(f.5) sliding said lens over the first eye of the user until said lens calibration target is in view through said pinhole aperture overlaying said viewing aperture;
(f.6) uncovering the second eye of the user; and
(f.7) removing said cover element from each said lens.

* * * * *